United States Patent [19]

VandenBerg

[11] Patent Number: Plant 7,511

[45] Date of Patent: Apr. 30, 1991

[54] CHRYSANTHEMUM PLANT NAMED DARK YELLOW FINA

[75] Inventor: Cornelis P. VandenBerg, Salinas, Calif.

[73] Assignee: Yoder Brothers, Inc., Barberton, Ohio

[21] Appl. No.: 435,823

[22] Filed: Nov. 14, 1989

[51] Int. Cl.[5] ..... A01H 5/00

[52] U.S. Cl. ..... Plt./74

[58] Field of Search ..... Plt./74; 42/58; 800/200

[56] References Cited

U.S. PATENT DOCUMENTS

P.P. 6,881 6/1989 VandenBerg ..... Plt./74

4,616,099 10/1986 Sparkes ..... 47/58

OTHER PUBLICATIONS

Searle, S. A., et al., "Breeding and Selection"; Appendix I *Chrysanthemums the Year Round,* Blandford Press, London, 1968, pp. 26–29; 320–327.

Gosling, S. G., "Appendix II Sporting and Irradiation", *The Chrysanthemum Manual,* Nat. Chrysanth. Soc., London, 1979, pp. 329–336.

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Dark Yellow Fina particularly characterized by its flat capitulum form; anemone to daisy capitulum type; yellow ray floret color; diameter across face of capitulum of up to 10 cm at maturity; uniform eight week photoperiodic flowering response to short days; peduncle length ranging from 8 to 20 cm on open, terminal sprays; medium plant height when grown as a single stem spray cut mum; and excellent tolerance to low temperatures for bud initiation and flower development.

1 Drawing Sheet

The present invention comprises a new and distinct cultivar of Chrysanthemum, botanically known as *Dendranthema grandiflora,* and referred to by the cultivar name Dark Yellow Fina.

Dark Yellow Fina, identified as 84-567A06, is a product of a mutation induction program which had the objective of creating new Chrysanthemum cultivars that would expand the color range of an existing cultivar while retaining all other traits.

Dark Yellow Fina was discovered and selected by Cornelis P. VandenBerg on Nov. 17, 1987 in a controlled environment in Salinas, Calif. as one flowering plant within a flowering block established as rooted cuttings from shock plants which had been exposed as unrooted cuttings to an X-ray source of 2000 rads. The irradiated parent was the cultivar identified as Fina, disclosed in U.S. Plant patent application Ser. No. 173,082.

The first act of asexual reproduction of Dark Yellow Fina was accomplished when vegetative cuttings were taken from the initial selection in January 1988 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Dark Yellow Fina are firmly fixed and are retained through successive generations of asexual reproduction.

Dark Yellow Fina has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice. The low temperature tolerance of the new variety as noted below was determined in repeated flowerings in Bogota, Colombia.

The following traits have been repeatedly observed and are determined to be basic characteristics of Dark Yellow Fina, which, in combination, distinguish this Chrysanthemum as a new and distinct cultivar:

1. Flat capitulum form.
2. Anemone to daisy capitulum type.
3. Yellow ray floret color.
4. Diameter across face of capitulum of up to 10 cm at maturity.
5. Uniform eight week photoperiodic flowering response to short days.
6. Peduncle length ranging from 8 to 20 cm on open, terminal sprays.
7. Medium plant height, requiring two long day weeks prior to short days to attain a flowered plant height of 90 to 100 cm for year-round flowerings.
8. Excellent tolerance to low temperatures for bud initiation and flower development.

The accompanying photographic drawing shows typical inflorescence and leaf characteristics of Dark Yellow Fina, with the colors being as nearly true as possible with illustrations of this type. The color photograph is a perspective view of Dark yellow Fina grown as a single stem cut spray mum.

Of the commercial cultivars known to the inventor, the most similar in comparison to Dark Yellow Fina is the parent cultivar Fina. All traits of Dark Yellow Fina are similar to those of Fina, except the color of the ray florets, the color of the anemone cushion and the flowering response to short days. The color of the ray florets of Dark Yellow Fina is yellow, whereas Fina has white ray florets. The anemone cushion of Dark Yellow Fina when mature is yellow, compared with the yellow-green anemone cushion of Fina. The flowering response of Dark Yellow Fina is two to three days slower than that of Fina.

In the following description color references are made to The Royal Horticultural Society Colour Chart. The color values were determined on plant material grown as a single stem cut spray mum in Salinas, Calif. on July 14, 1989.

Classification:

*Botanical.*—*Dendranthema grandiflora* cv Dark Yellow Fina.

*Commercial.*—Anemone to daisy cut spray mum.

INFLORESCENCE

A. Capitulum:

*Form.*—Flat.

*Type.*—Anemone to daisy. Anemone cushion is small and slow in development, and capitulum type is close to daisy.

*Diameter across face.*—Up to 10 cm at maturity.

*Diameter of anemone cushion.*—Up to 2 cm.

B. Corolla of ray florets:

*Color (general tonality from a distance of three meters).*—Yellow.

*Color (upper surface).*—6A to 6B.

*Color (under surface).*—Margins 6D, center 6C.

*Shape.*—Flat, oblong. Older flowers show longitudinal petal twist.

C. Corolla of disc florets:

*Color (mature).*—Closest to 6A; since the disc florets in the photograph have not yet matured, the mature color is visible only at the periphery of certain of the discs.

*Color (immature).*—Closest to 143B.

D. Reproductive organs:

*Androecium.*—Present on disc florets only; scant pollen.

*Gynoecium.*—Present on both ray and disc florets.

PLANT

A. General appearance:

*Height.*—Medium; 90 to 100 cm as a single stem cut mum with two long day weeks prior to short days.

B. Foliage:

*Color (upper surface).*—147A.

*Color (under surface).*—147B.

*Shape.*—Lobed, slightly serrated.

I claim:

1. A new and distinct Chrysanthemum plant named Dark Yellow Fina, as described and illustrated.

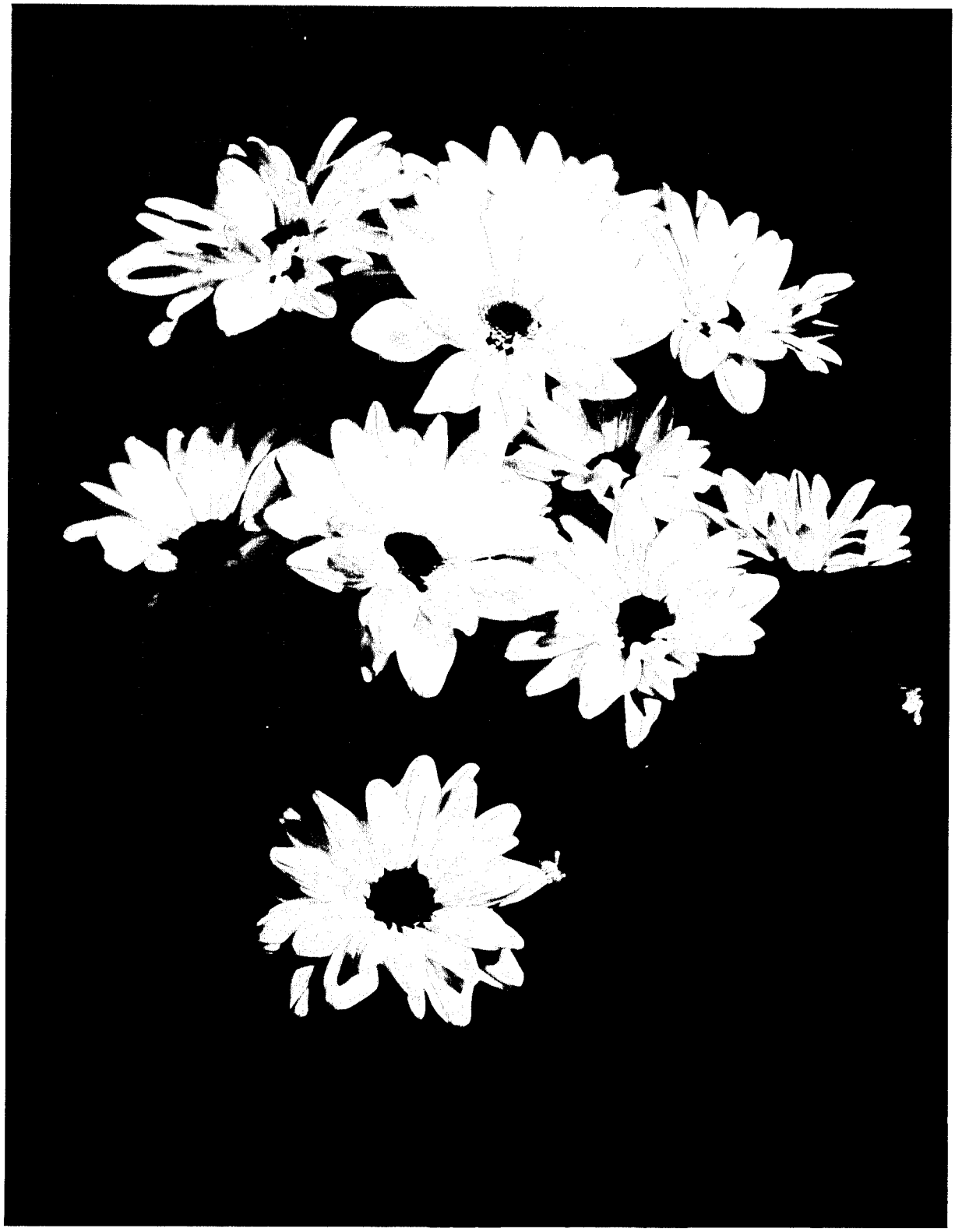

* * * * *